(12) United States Patent
Ross et al.

(10) Patent No.: US 11,207,091 B2
(45) Date of Patent: Dec. 28, 2021

(54) SURGICAL INSTRUMENT FOR GRASPING, TREATING, AND/OR DIVIDING TISSUE

(71) Applicant: COVIDIEN LP, Mansfield, MA (US)

(72) Inventors: Anthony B. Ross, Boulder, CO (US); Eric R. Larson, Boulder, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 463 days.

(21) Appl. No.: 15/798,455

(22) Filed: Oct. 31, 2017

(65) Prior Publication Data

US 2018/0125517 A1 May 10, 2018

Related U.S. Application Data

(60) Provisional application No. 62/418,997, filed on Nov. 8, 2016.

(51) Int. Cl.
*A61B 17/295* (2006.01)
*A61B 17/29* (2006.01)
(Continued)

(52) U.S. Cl.
CPC .......... *A61B 17/295* (2013.01); *A61B 1/0008* (2013.01); *A61B 17/2909* (2013.01); *A61B 18/1445* (2013.01); *A61B 1/00133* (2013.01); *A61B 1/05* (2013.01); *A61B 17/0469* (2013.01); *A61B 17/3417* (2013.01); *A61B 17/3462* (2013.01); *A61B 2017/00358* (2013.01); *A61B 2017/00738* (2013.01); *A61B 2017/2901* (2013.01); *A61B 2017/294* (2013.01);
(Continued)

(58) Field of Classification Search
CPC ..... A61B 17/28; A61B 17/2812; A61B 17/29; A61B 2017/2901; A61B 2017/2908; A61B 2017/2945; A61B 2017/2948
See application file for complete search history.

(56) References Cited

U.S. PATENT DOCUMENTS 702,472 A 6/1902 Pignolet
2,801,633 A 8/1957 Ehrlich
(Continued)

FOREIGN PATENT DOCUMENTS

CN 100493469 C 6/2009
CN 101516285 A 8/2009
(Continued)

*Primary Examiner* — Todd J Scherbel
(74) *Attorney, Agent, or Firm* — Carter, DeLuca & Farrell LLP

(57) ABSTRACT

A surgical instrument includes a housing, an end effector assembly, and a shaft. The end effector assembly includes first and second jaw members each defining a curved configuration. At least one of the jaw members is movable relative to the other between a spaced-apart position and an approximated position. The shaft includes a proximal portion coupled with and extending distally from the housing and a distal portion extending distally from the proximal portion and having the end effector assembly coupled thereto at the distal end thereof. The proximal portion defines a circular cross-sectional configuration to facilitate formation of a fluid-tight seal thereabout. The distal portion defines a rectangular cross-sectional configuration configured to facilitate insertion through a cannula.

20 Claims, 11 Drawing Sheets

(51) Int. Cl.
  *A61B 1/00* (2006.01)
  *A61B 18/14* (2006.01)
  *A61B 17/00* (2006.01)
  *A61B 17/04* (2006.01)
  *A61B 17/34* (2006.01)
  *A61B 1/05* (2006.01)

(52) U.S. Cl.
  CPC .......... *A61B 2017/2929* (2013.01); *A61B 2017/2945* (2013.01); *A61B 2018/1452* (2013.01)

(56) References Cited

U.S. PATENT DOCUMENTS

| | | | |
|---|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| 4,793,218 A | 12/1988 | Jordan et al. |
| D299,413 S | 1/1989 | DeCarolis |
| 5,100,506 A | 3/1992 | Sturtevant et al. |
| 5,242,456 A | 9/1993 | Nash et al. |
| D343,453 S | 1/1994 | Noda |
| 5,302,234 A | 4/1994 | Grace et al. |
| 5,317,938 A | 6/1994 | de Juan, Jr. et al. |
| D348,930 S | 7/1994 | Olson |
| D349,341 S | 8/1994 | Lichtman et al. |
| D354,564 S | 1/1995 | Medema |
| 5,383,471 A | 1/1995 | Funnell |
| 5,395,364 A | 3/1995 | Anderhub et al. |
| D358,887 S | 5/1995 | Feinberg |
| 5,431,667 A | 7/1995 | Thompson et al. |
| 5,486,185 A | 1/1996 | Freitas et al. |
| 5,486,189 A | 1/1996 | Mudry et al. |
| 5,522,830 A | 6/1996 | Aranyi |
| 5,522,839 A | 6/1996 | Pilling |
| 5,539,973 A | 7/1996 | Smith et al. |
| 5,571,129 A | 11/1996 | Porter |
| 5,620,447 A | 4/1997 | Smith et al. |
| 5,626,609 A | 5/1997 | Zvenyatsky et al. |
| D384,413 S | 9/1997 | Zlock et al. |
| 5,707,392 A | 1/1998 | Kortenbach |
| 5,716,374 A | 2/1998 | Francese et al. |
| H1745 H | 8/1998 | Paraschac |
| 5,833,692 A | 11/1998 | Cesarini et al. |
| D402,028 S | 12/1998 | Grimm et al. |
| D408,018 S | 4/1999 | McNaughton |
| D416,089 S | 11/1999 | Barton et al. |
| 6,013,028 A | 1/2000 | Jho et al. |
| D424,694 S | 5/2000 | Tetzlaff et al. |
| D425,201 S | 5/2000 | Tetzlaff et al. |
| 6,117,158 A | 9/2000 | Measamer et al. |
| H1904 H | 10/2000 | Yates et al. |
| 6,202,465 B1 | 3/2001 | Jankoski et al. |
| 6,277,117 B1 | 8/2001 | Tetzlaff et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| 6,790,217 B2 * | 9/2004 | Schulze .......... A61B 18/1445 606/171 |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,101,371 B2 | 9/2006 | Dycus et al. |
| D531,311 S | 10/2006 | Guerra et al. |
| 7,122,035 B2 | 10/2006 | Canady |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| 7,186,261 B2 | 3/2007 | Prestel |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,267,677 B2 | 9/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,968,311 B2 | 3/2015 | Allen, IV et al. |
| 9,375,263 B2 | 6/2016 | Allen, IV et al. |
| 2002/0058925 A1 | 5/2002 | Kaplan et al. |
| 2002/0161364 A1 | 10/2002 | Mulier et al. |
| 2004/0148992 A1 | 8/2004 | Huang |
| 2005/0240218 A1 | 10/2005 | Freed et al. |
| 2008/0083257 A1 | 4/2008 | Taylor et al. |
| 2008/0264139 A1 | 10/2008 | Rosenbohm et al. |
| 2008/0319467 A1 | 12/2008 | Wenchell |
| 2009/0088743 A1 | 4/2009 | Masuda |
| 2009/0182327 A1 | 7/2009 | Unger |
| 2010/0145334 A1 | 6/2010 | Olson et al. |
| 2011/0009864 A1 | 1/2011 | Bucciaglia et al. |
| 2011/0144665 A1 | 6/2011 | Malkowski |
| 2013/0296848 A1 * | 11/2013 | Allen, IV .......... A61B 18/1445 606/41 |
| 2015/0289863 A1 * | 10/2015 | Sauer .......... A61B 17/00234 606/144 |

FOREIGN PATENT DOCUMENTS

| | | |
|---|---|---|
| CN | 201299462 Y | 9/2009 |
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 A1 | 8/1994 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102008018406 B3 | 7/2009 |
| EP | 0584787 A1 | 3/1994 |
| EP | 1159926 A2 | 12/2001 |
| EP | 1810625 A1 | 7/2007 |

(56) References Cited

FOREIGN PATENT DOCUMENTS

| | | |
|---|---|---|
| EP | 2347725 A1 | 7/2011 |
| EP | 2399538 A2 | 12/2011 |
| EP | 2574299 A2 | 4/2013 |
| JP | 61-501068 | 9/1984 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | H08-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 910223 | 1/1997 |
| JP | 9-122138 A | 5/1997 |
| JP | 0010000195 A | 1/1998 |
| JP | H10-24051 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 2001-8944 | 1/2001 |
| JP | 2001029356 A | 2/2001 |
| JP | 2001128990 A | 5/2001 |
| JP | 2001190564 A | 7/2001 |
| JP | 2001-003400 | 11/2001 |
| JP | 2002136525 A | 5/2002 |
| JP | 2002528166 A | 9/2002 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 05110264 A3 | 4/2006 |
| WO | 2010014825 A1 | 2/2010 |

\* cited by examiner

SURGICAL INSTRUMENT FOR GRASPING, TREATING, AND/OR DIVIDING TISSUE

CROSS REFERENCE TO RELATED APPLICATION

The present application claims the benefit of and priority to U.S. Provisional Application Ser. No. 62/418,997, filed on Nov. 8, 2016 the entire contents of which are incorporated herein by reference.

BACKGROUND

Technical Field

The present disclosure relates generally to the field of surgical instruments. In particular, the disclosure relates to a surgical instrument for grasping, treating, and/or dividing tissue.

Background of Related Art

Various different surgical instruments are utilized for grasping, treating, and/or dividing tissue. A surgical forceps, for example, is a pliers-like surgical instrument that relies on mechanical action between its jaw members to grasp, clamp, and constrict tissue. Energy-based surgical forceps utilize both mechanical clamping action and energy, e.g., radiofrequency (RF) energy, microwave energy, ultrasonic energy, light energy, thermal energy, etc., to heat tissue to treat, e.g., coagulate, cauterize, and/or seal, tissue.

Typically, once tissue is treated, the surgeon has to accurately divide the treated tissue. Accordingly, many surgical forceps are designed to incorporate a knife or cutting member utilized to effectively divide the treated tissue.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein.

Provided in accordance with aspects of the present disclosure is a surgical instrument including a housing, an end effector assembly, and a shaft. The end effector assembly includes first and second jaw members each defining a curved configuration. One or both of the jaw members is movable relative to the other between a spaced-apart position and an approximated position. The shaft extends between the housing and the end effector assembly and includes a proximal portion and a distal portion. The proximal portion of the shaft is coupled with and extends distally from the housing. The proximal portion of the shaft defines a circular cross-sectional configuration to facilitate formation of a fluid-tight seal thereabout. The distal portion of the shaft extends distally from the proximal portion to a distal end, wherein the end effector assembly is coupled thereto. The distal portion of the shaft defines a rectangular cross-sectional configuration to facilitate insertion through a cannula.

In an aspect of the present disclosure, the shaft is an integral, rigid component.

In another aspect of the present disclosure, the shaft further includes an intermediate portion interconnecting the proximal portion and the distal portion. The intermediate portion may define a smooth, continuous transition between the proximal portion and the distal portion.

In yet another aspect of the present disclosure, the distal portion of the shaft defines a pair of opposed long sides and a pair of opposed short sides.

In still another aspect of the present disclosure, the first and second jaw members curve towards one of the opposed long sides of the distal portion of the shaft.

In still yet another aspect of the present disclosure, the lengths of the opposed long sides of the distal portion of the shaft approximate a diameter of the proximal portion of the shaft and/or the lengths of the opposed short sides of the distal portion of the shaft are less than a diameter of the proximal portion of the shaft.

In another aspect of the present disclosure, the distal portion of the shaft is offset relative to the proximal portion of the shaft. Alternatively, the distal portion of the shaft may be aligned with the proximal portion of the shaft.

Also provided in accordance with aspects of the present disclosure is a surgical system including a surgical instrument and a cannula. The cannula includes a housing, an elongated sleeve extending distally from the housing, and a seal member disposed within the housing. The surgical instrument is configured for insertion at least partially through the cannula and includes a housing, an end effector assembly, and a shaft. The end effector assembly includes first and second jaw members each defining a curved configuration. The first and/or second jaw member is movable relative to the other between a spaced-apart position and an approximated position. The shaft extends between the housing and the end effector assembly and includes a proximal portion and a distal portion. The proximal portion of the shaft is coupled with the housing, extends distally from the housing, and defines a circular cross-sectional configuration. The seal member of the cannula is configured to form a fluid-tight seal about the proximal portion of the shaft upon insertion of the surgical instrument at least partially through the cannula. The distal portion of the shaft extends distally from the proximal portion to a distal end, wherein the end effector assembly is coupled thereto. The distal portion of the shaft defines a rectangular cross-sectional configuration to facilitate insertion of the curved first and second jaw members through the cannula.

In an aspect of the present disclosure, the shaft is an integral, rigid component.

In another aspect of the present disclosure, the shaft further includes an intermediate portion interconnecting the proximal portion and the distal portion. The intermediate portion may define a smooth, continuous transition between the proximal portion and the distal portion to facilitate insertion of the shaft through the seal member of the cannula.

In still another aspect of the present disclosure, the cannula defines a lumen extending therethrough. In such aspects, the lumen has a first length and the distal portion of the shaft and the end effector assembly collectively define a second length that is equal to or greater than the first length.

In yet another aspect of the present disclosure, the first and second lengths are relatively configured such that, when the surgical instrument is inserted through the cannula with the end effector assembly of the surgical instrument extending distally from the cannula, the seal member of the cannula forms a fluid-tight seal about the proximal portion of the shaft of the surgical instrument.

In still yet another aspect of the present disclosure, the distal portion of the shaft of the surgical instrument defines a pair of opposed long sides and a pair of opposed short sides. In such aspects, the first and second jaw members of the end effector assembly curve towards one of the opposed long sides of the distal portion of the shaft.

In another aspect of the present disclosure, the cannula defines a lumen extending therethrough. The lumen has a diameter and the proximal portion of the shaft and the end effector assembly of the surgical instrument collectively define a maximum width dimension that is equal to or greater than the diameter of the lumen of the cannula.

In another aspect of the present disclosure, the surgical instrument is configured for insertion through the lumen of the cannula in an angled orientation relative to the lumen of the cannula to accommodate the curved first and second jaw members.

In yet another aspect of the present disclosure, the distal portion of the shaft is offset relative to the proximal portion of the shaft. Alternatively or additionally, the distal portion of the shaft may be aligned with the proximal portion of the shaft.

BRIEF DESCRIPTION OF THE DRAWINGS

Various aspects and features of the present disclosure are described herein with reference to the drawings, wherein like reference numerals identify similar or identical components, and wherein.

DETAILED DESCRIPTION

Figure 1:
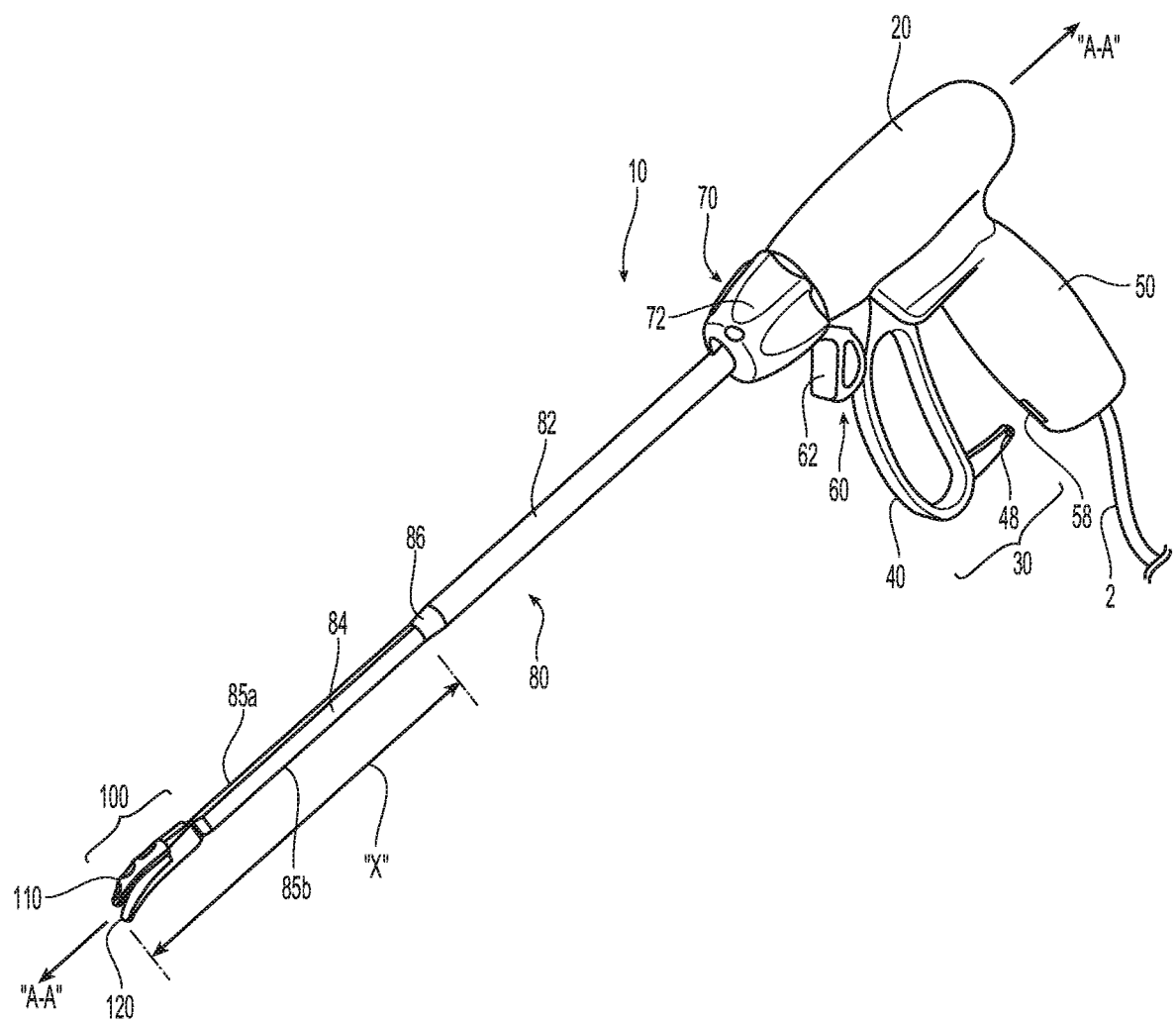
FIG. 1 is a perspective view of an endoscopic surgical forceps provided in accordance with aspects of the present disclosure.

Referring generally to FIG. 1, an endoscopic surgical forceps provided in accordance with the present disclosure is shown generally identified by reference numeral 10. As described in greater detail below, forceps 10 is configured for insertion through a cannula 200 (FIG. 2) and into an internal surgical site for grasping tissue, treating the grasped tissue with energy, and dividing the grasped and/or treated tissue. Although detailed herein with respect to endoscopic forceps 10, the aspects and features of the present disclosure are equally applicable for use with any suitable surgical instrument.

Figure 6A:
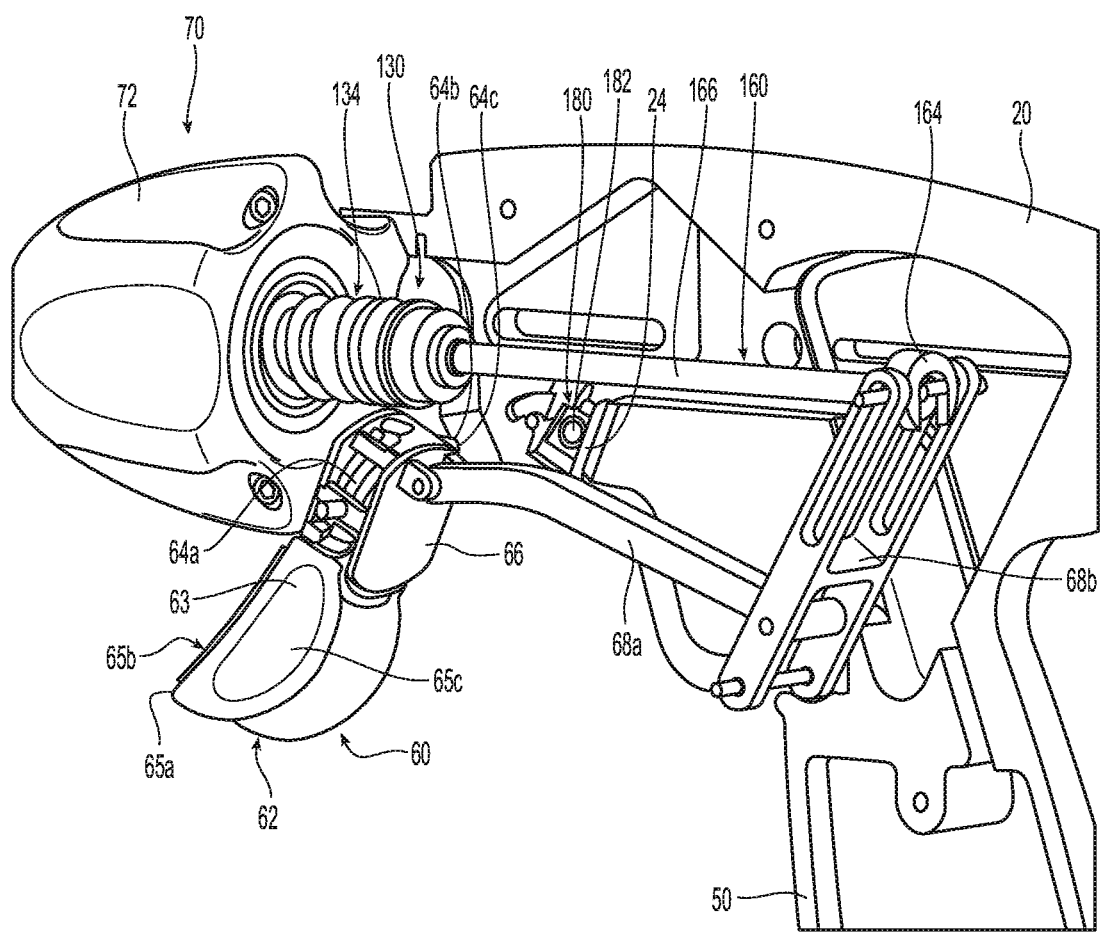
FIG. 6A is a perspective, exploded view of another proximal portion of the surgical forceps of FIG. 1, with components removed.
Figure 6B:
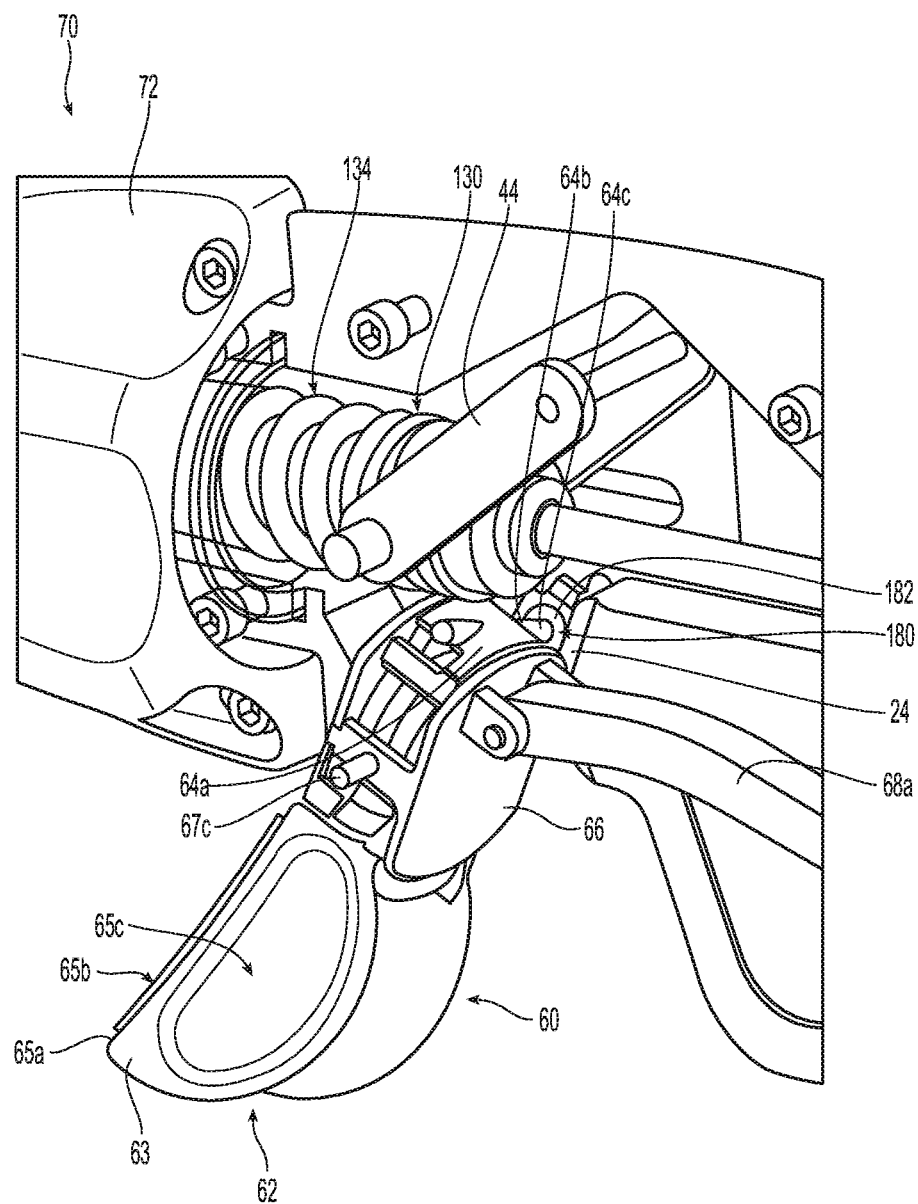
FIG. 6B is a perspective view of another proximal portion of the surgical forceps of FIG. 1, with components removed.
Figure 6C:
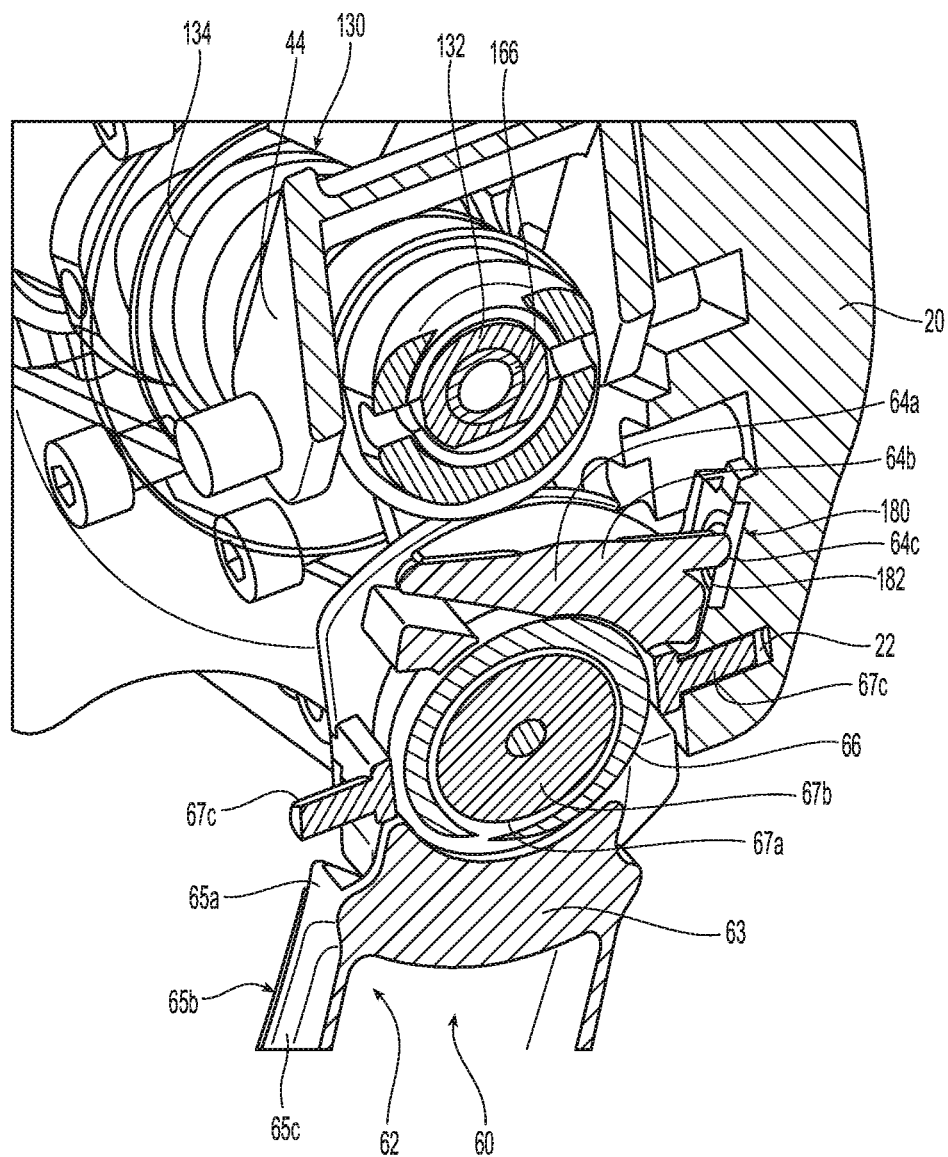
FIG. 6C is a perspective, transverse, cross-sectional view taken through another proximal portion of the surgical forceps of FIG. 1, with components removed.

With reference to FIGS. 1 and 4-8B, forceps 10 generally includes a housing 20, a handle assembly 30, a trigger assembly 60, a rotation assembly 70, a shaft 80, an end effector assembly 100, a drive assembly 130 (FIGS. 6A-6C), a knife assembly 160 (FIGS. 6A and 8B), and an activation assembly 180 (FIGS. 6A-6C). Forceps 10 further includes a cable 2 configured to couple forceps 10 to a source of energy, e.g., an electrosurgical generator (not shown), for supplying energy to end effector assembly 100, although forceps 10 may alternative be configured as a cordless, hand-held device. The components and assemblies of forceps 10 are described more generally, followed by a more detailed description of the components and assemblies of forceps 10 that are germane to the aspects and features of the present disclosure.

Handle assembly 30 is operably coupled to housing 20 and includes a movable handle 40 extending from housing 20 adjacent fixed handle portion 50 of housing 20 to permit manual manipulation of movable handle 40 by a user. Trigger assembly 60 is also operably coupled to housing 20 and similarly includes a trigger 62 extending from housing 20 to permit manual manipulation thereof by a user.

Shaft 80 extends distally from housing 20, defines a longitudinal axis "A-A," and includes end effector assembly 100 disposed towards the distal end thereof. Shaft 80 may be configured as an integral, rigid component. Rotation assembly 70 may be disposed about the distal end of housing 20 and operably coupled to shaft 80 such that rotation of rotation nose 72 of rotation assembly 70 rotates shaft 80 and end effector assembly 100 relative to housing 20.

End effector assembly 100 includes first and second jaw members 110, 120, at least one of which is movable relative to the other and shaft 80 between a spaced-apart position and an approximated position. Drive assembly 130 (FIGS. 6A-6C) extends through housing 20 and shaft 80 and operably couples movable handle 40 of handle assembly 30 with end effector assembly 100 such that movement of movable handle 40 moves jaw members 110, 120 between the spaced-apart and approximated positions.

Figure 8A:
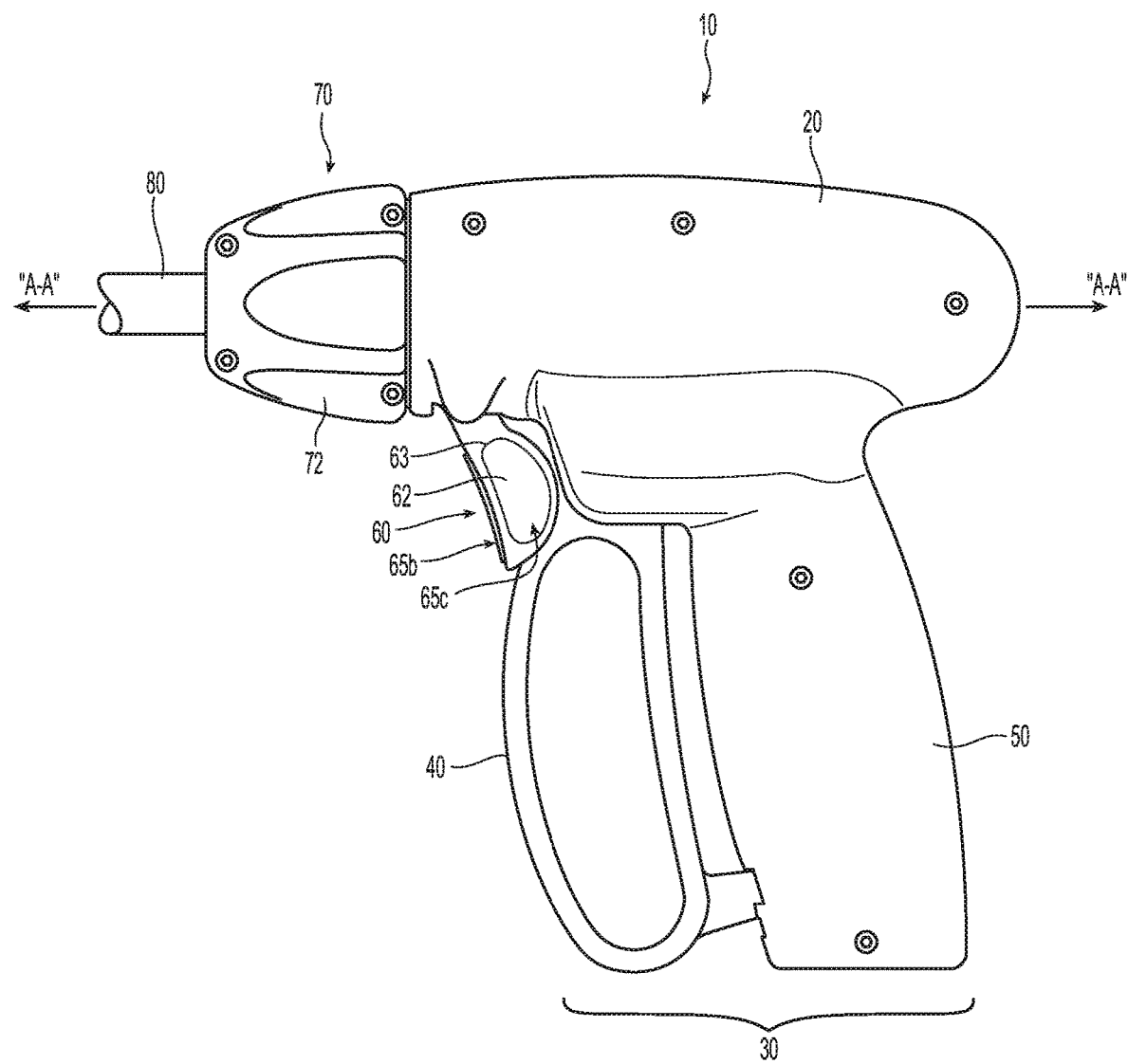
FIG. 8A is a side view of a proximal portion of the surgical forceps of FIG. 1, with the handle disposed in a compressed position and the trigger disposed in an actuated position.
Figure 8B:
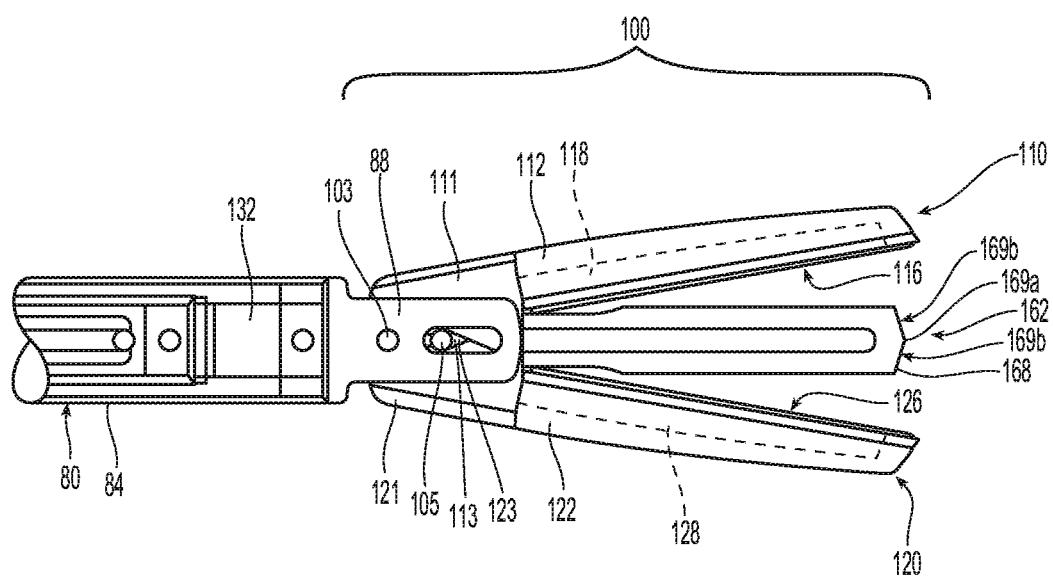
FIG. 8B is a side view of the end effector assembly of the surgical forceps of FIG. 1 with the knife disposed in an extended position corresponding to the actuated position of the trigger of FIG. 8A.

Knife assembly 160 (FIG. 6A) includes a knife 162 (FIG. 8B) slidably disposed within shaft 80 and operably coupled to trigger 62 of trigger assembly 60 such that actuation of trigger 62 advances knife 162 from a retracted position, wherein knife 162 is disposed proximally of end effector assembly 100, to an extended position, wherein knife 162 extends between jaw members 110, 120 (see FIG. 8B). With particular reference to FIG. 8B, knife 162 includes a distal cutting edge 168 having a dual-rake configuration defining a central protruding point 169a and angled cutting edges 169b angled proximally from central protruding point 169a. As a result of this configuration, upon advancement of knife 162, distal cutting edge 168 is led by central protruding point 169a, which is the distal-most portion of knife 162 and is positioned between jaw members 110, 120, while angled extend proximally from central protruding point 169a at least partially into the knife channels 118, 128 of jaw members 110, 120, respectively. It is noted that jaw members 110, 120 are shown in a partially-open condition in FIG.

8B to permit visualization of knife 162 and, thus, knife 162 is not shown positioned within knife channels 118, 128. However, with jaw members 110, 120 in the approximated position upon advancement of knife 162, the above-detailed configuration is achieved.

Referring again to FIGS. 1 and 4-8B, activation assembly 180 (FIGS. 6A-6C) includes a pair of switches 182 (FIGS. 6A-6C; only one switch 182 is shown) disposed within housing 20 and operably associated with trigger 62 of trigger assembly 60 such that activation of trigger 62 depresses one of switches 182 (depending upon the direction of activation of trigger 62) to supply energy from the energy source to jaw members 110, 120 of end effector assembly 100. Cable 2 includes a plurality of lead wires (not explicitly shown) extending therethrough. The lead wires extend through housing 20 and shaft 80 to electrically couple the energy source, switches 182 of activation assembly 180, and electrically-conductive surfaces 116, 126 of jaw members 110, 120 with one another.

Figure 2:
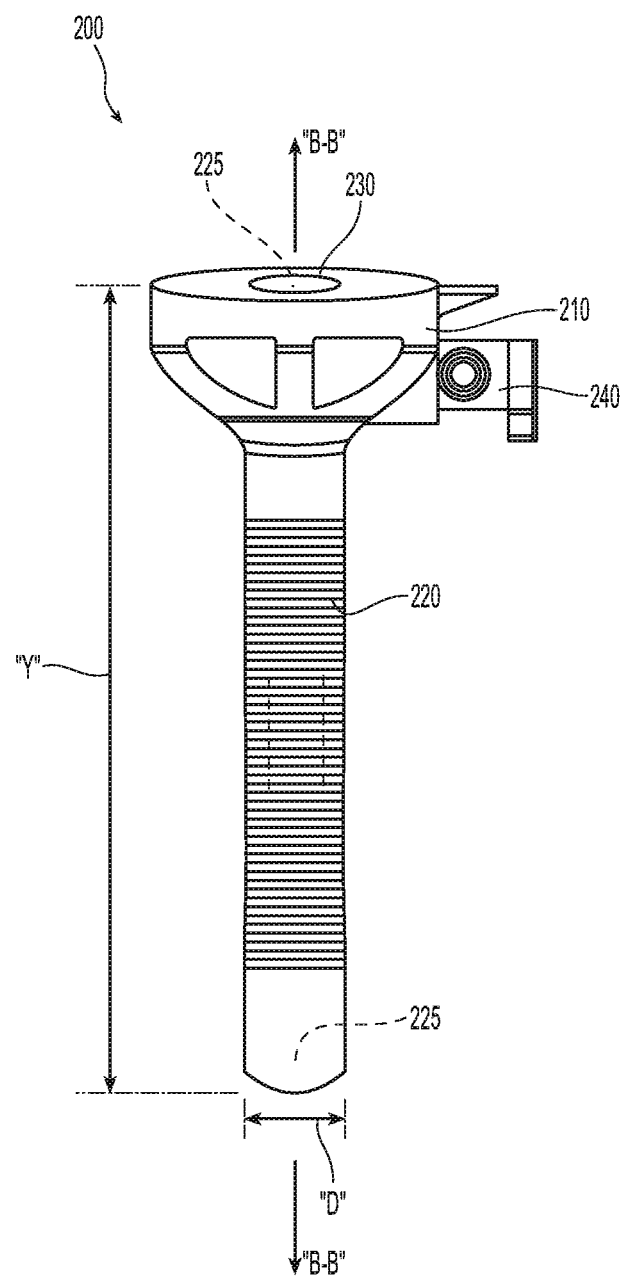
FIG. 2 is a perspective view of a cannula configured for use with the surgical forceps of FIG. 1.
Figure 3:
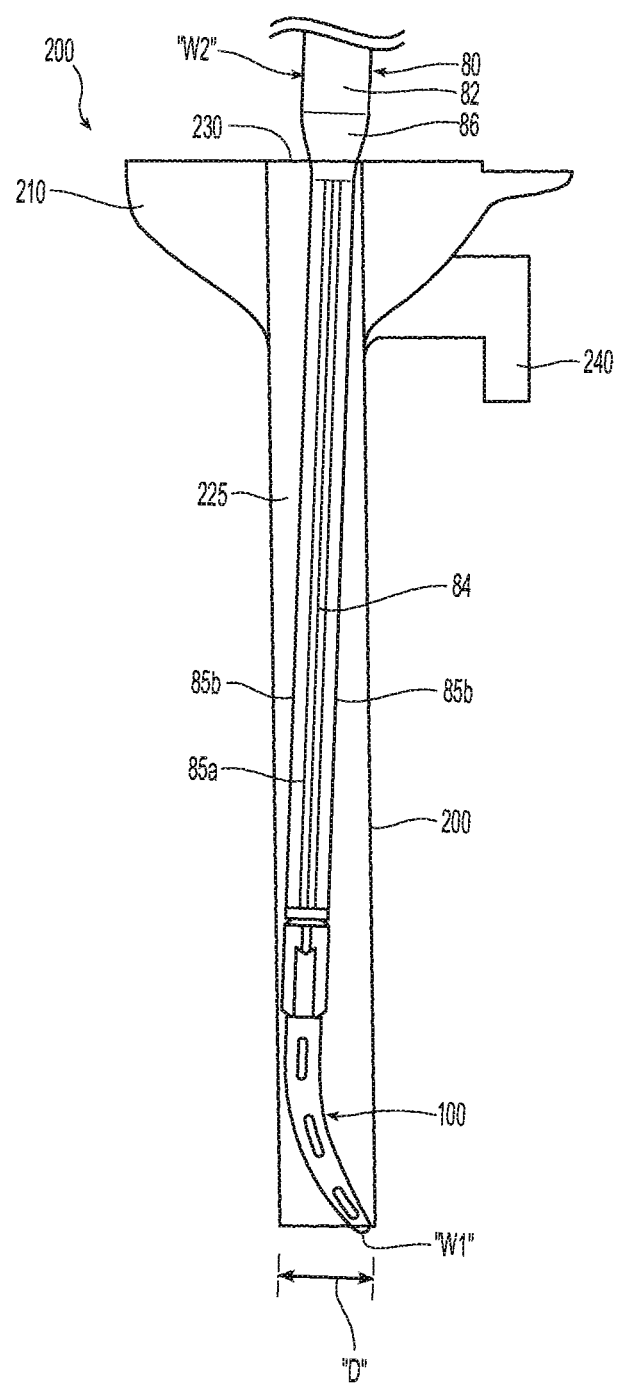
FIG. 3 is a side, partial cross-sectional view illustrating insertion of a distal portion of the surgical forceps of FIG. 1 through the cannula of FIG. 2.

With additional reference to FIGS. 2 and 3, forceps 10 is configured for use in endoscopic surgical procedures (although forceps 10 may equally be used in traditional open surgical procedures) and, thus, shaft 80 and jaw members 110, 120 of end effector assembly 100 are configured for insertion through a cannula 200 to facilitate access to an internal surgical site. Shaft 80 defines longitudinal axis "A-A and includes a proximal portion 82, a distal portion 84, and a transition portion 86 between proximal and distal portions 82, 84 where shaft 80 transitions from proximal portion 82 to distal portion 84. Proximal portion 82 of shaft 80 defines a circular cross-sectional configuration, which provides strength and support to shaft 80. The circular cross-sectional configuration of proximal portion 82, being smooth, continuous, without angles or edges, and radially-symmetric, also facilitates formation of a fluid-tight seal about proximal portion 82, e.g., via seal member 230 of cannula 200, upon insertion into cannula 200.

Distal portion 84 of shaft 80 and end effector assembly 100 cooperate to define a length "X" that is less than the overall cooperative length of shaft 80 and end effector assembly 100. Distal portion 84 defines a rectangular cross-sectional configuration including a pair of opposed short sides 85a and a pair of opposed long sides 85b. Each of the opposed long sides 85b of distal portion 84 of shaft 80 defines a width that approximates the diameter of the circular cross-sectional proximal portion 82 of shaft 80, although other configurations are also contemplated. Each of the opposed short sides 85a of distal portion 84 of shaft 80 defines a width that is less than a diameter of the circular cross-sectional proximal portion 82 of shaft 80 such that distal portion 84 of shaft 80 defines a narrowed configuration as compared to proximal portion 82 of shaft 80. This narrowed configuration facilitates visualization of end effector assembly 100 and insertion of end effector assembly 100 and shaft 80 through cannula 200 and into an internal surgical site, as detailed below. Further, the narrowed configuration of distal portion 84 of shaft 80 allows for positioning of other instrumentation, e.g., irrigation and/or suction tubes, a camera, a sensor(s), a light source, an energizable probe, a navigation tool, etc. alongside distal portion 84 of shaft 80 without extending beyond or extending minimally beyond the outer dimension of proximal portion 82 of shaft 80. The additional instrumentation may be incorporated into forceps 10, e.g., extending through proximal portion 82 of shaft 80 and alongside distal portion 84 of shaft 80, may be releasably engagable with distal portion 84 of shaft 80, or may be wholly separate from forceps 10.

Distal portion 84 of shaft 80 may be centered relative to the longitudinal axis "A-A" of shaft 80 or may be offset relative thereto, e.g., such that one of the long sides 85b is closer to the longitudinal axis "A-A" than the other long side 85b. Further, other narrowed configurations, e.g., square, oval, semi-circle, smaller-diametered circle, etc., are also contemplated. Intermediate portion 86 of shaft 80 provides a smooth, continuous transition between proximal and distal portions 82, 84, respectively, thus inhibiting potential snag points along shaft 80 and facilitating insertion thereof into and through cannula 200.

End effector assembly 100, as noted above, includes first and second jaw members 110, 120. Jaw members 110, 120 define curved configurations, wherein jaw members 110, 120 curve off of the longitudinal axis "A-A" of shaft 80 towards one of the long sides 85b of distal portion 84 of shaft 80 (and away from the other long side 85b of distal portion 84 of shaft 80). Jaw members 110, 120 are sufficiently curved such that the distal ends of jaw members 110, 120 extend beyond the outer dimension of the circular cross-sectional proximal portion 82 of shaft 80. Thus, the maximum width dimension defined by shaft 80 and end effector assembly 100 extends transversely from the distal tips "W1" of jaw members 110, 120 to the outer-most dimension of the opposite side "W2" of proximal portion 82 of shaft 80 (see FIG. 3). The curved configurations of jaw members 110, 120 of end effector assembly 100 facilitate visualization of tissue as tissue is grasped, manipulated, treated, and/or divided. In configurations where distal portion 84 of shaft 80 is offset relative to the longitudinal axis "A-A" of shaft 80, jaw members 110, 120 are configured to curve away from the offset direction of distal portion 84, thus reducing the maximum width dimension of shaft 80 and end effector assembly 100.

Referring to FIGS. 2 and 3, an exemplary cannula 200 configured for use in endoscopic surgery is shown defining a longitudinal axis "B-B" and generally including a proximal housing 210, a distal sleeve 220 extending from proximal housing 210, at least one seal member 230, and a fluid port 240 defined therein. Although exemplary cannula 200 is shown and described herein, it is understood that the aspects and features of the present disclosure apply equally to any suitable cannula providing access to an internal surgical site. Proximal housing 210 is configured for positioning on the exterior surface of a patient's skin and includes seal member 230 disposed therein. Proximal housing 210, distal sleeve 220, and seal member 230 cooperate to define a lumen 225 extending therethrough. Seal member 230 is configured to establish a fluid-tight seal about an instrument or instruments, e.g., proximal portion 82 of shaft 80 of forceps 10 (FIG. 1), inserted through lumen 225 of cannula 200. Seal member 230 may be any suitable seal or combination of seals, e.g., a duck bill valve, brush seal, elastomeric seal, etc., for establishing a fluid-tight seal about an instrument or instruments. Fluid port 240 is configured to connect to a fluid supply for insufflating the internal surgical site, providing other fluid thereto, or removing fluid therefrom. Cannula 200 defines a length "Y" and lumen 225 of cannula 200 defines a diameter "D." Further, plural cannulas 200 may be provided of different lengths and/or diameters, such that an appropriate cannula 200 may be selected based upon a patient's anatomy, the procedure to be performed, preference of the user, and/or other factors. To this end, plural forceps 10 may be provided, each configured for use with one or more of the different length and/or diameter cannulas 200. It is typically advantageous to use the smallest-diametered cannula 200 suitable for the particular patient and/or procedure as such requires a smaller incision for the cannula 200 and, as a result, reduced post-surgical pain and healing time. However, other factors and/or considerations may warrant use of a different cannula 200.

Referring to FIG. 3, as noted above, shaft 80 and end effector assembly 100 are configured for insertion through cannula 200 and into an internal surgical site. Where plural size cannulas 200 and/or forceps 10 (FIG. 1) with plural size shafts 80 are provided, a suitable cannula 200 and forceps 10 (FIG. 1) pair is first selected. In an effort to utilize the smallest-diameter cannula 200, it is contemplated that the cannula 200 and forceps 10 (FIG. 1) pair be configured such that the length "Y" of the cannula 200 is equal to the collective length "X" of distal portion 84 of shaft 80 and end effector assembly 100 or less than the collective length "X" but sufficiently long so as to ensure that seal member 230 is disposed about proximal portion 82 of shaft 80 when end effector assembly 100 is positioned within the internal surgical site (rather than being disposed about transition portion 86 or distal portion 84, where it may be more difficult to establish an effective seal). For similar purposes, it is further contemplated that cannula 200 and forceps 10 (FIG. 1) be configured such that the diameter "D" of lumen 225 of cannula 200 is equal to or greater than the maximum width dimension defined by shaft 80 and end effector assembly 100 but sufficiently small to enable insertion of end effector assembly 100 and shaft 80 therethrough in an angled orientation relative to distal sleeve 220 of cannula 200.

In use, cannula 200 is positioned within an opening in tissue such that proximal housing 210 remains external while distal sleeve 220 extends through the opening in tissue into the internal surgical site. When forceps 10 (FIG. 1) is to be used, end effector assembly 100 and shaft 80 are inserted through lumen 225 of cannula 200. As a result of the above-noted length and width/diameter relationship, end effector assembly 100 and distal portion 84 of shaft 80 are inserted through lumen 225 of cannula 200 in an angled orientation relative to longitudinal axis "B-B" of cannula 200. This configuration enables insertion of end effector 100 and distal portion 84 of shaft 80 through lumen 225 of cannula 220 despite diameter "D" of lumen 225 of cannula 200 being equal to or greater than the maximum width dimension defined by shaft 80 and end effector assembly 100. As end effector assembly 100 and shaft 80 are further inserted through lumen 225 of cannula 200, the distal tips "W1" of jaw members 110, 120 eventually reach the distal end of distal sleeve 220 of cannula 200. As a result of the length "Y" of the cannula 200 being equal to or less than the collective length "X" of distal portion 84 of shaft 80 and end effector assembly 100, the distal tips "W1" of jaw members 110, 120 reach the distal end of distal sleeve 220 prior to transition portion 86 of shaft 80 entering lumen 225 of cannula 200. Thus, upon further insertion of end effector assembly 100 and shaft 80 into cannula 200, curved jaw members 110, 120 begin to emerge from the distal end of distal sleeve 220, allowing shaft 80 to be straightened from the angled orientation towards an aligned orientation relative to longitudinal axis "B-B" of cannula 200, thereby providing sufficient clearance for transition portion 86 and, ultimately, proximal portion 82 of shaft 80 to enter lumen 225 of cannula 200 to permit further insertion of end effector assembly 100 and shaft 80 into and through cannula 200 such that end effector assembly 100 may be readily positioned at the internal surgical site.

With end effector assembly 100 positioned at the internal surgical site, at least a portion of proximal portion 82 of shaft 80 has entered cannula 200 such that seal member 230 is disposed about the circular cross-sectional proximal portion 82 of shaft 80, thus ensuring an effective fluid-tight seal. Once this position has been achieved, forceps 10 (FIG. 1) may be utilized to grasp, treat, and/or divide tissue, as detailed below.

Referring to FIGS. 1 and 8B, end effector assembly 100, as mentioned above, includes first and second jaw members 110, 120. Jaw members 110, 120 are pivotably coupled to one another and shaft 80 to enable movement of jaw members 110, 120 relative to one another and shaft 80 between the spaced-apart position and the approximated position. As an alternative to this bilateral configuration, end effector assembly 100 may define a unilateral configuration, e.g., wherein jaw member 120 is fixed relative to shaft 80 and jaw member 110 is pivotable relative to jaw member 120 and shaft 80 between the spaced-apart and approximated positions.

Each jaw member 110, 120 of end effector assembly 100 includes a proximal flange 111, 121 and a distal body 112, 122. Proximal flanges 111, 121 define aligned pivot apertures (not shown) and oppositely-angled cam slots 113, 123. The pivot apertures are configured to receive a pivot pin 103 for pivotably coupling jaw members 110, 120 to clevis 88 of distal portion 86 of shaft 80. Oppositely-angled cam slots 113, 123 receive a drive pin 105 that is operably coupled to drive bar 132 of drive assembly 130 (FIGS. 6A-6C) such that translation of drive bar 132 through shaft 80 and relative to end effector assembly 100 pivots jaw members 110, 120 between the spaced-apart and approximated positions.

Distal bodies 112, 122 of jaw members 110, 120 each define a curved configuration, as noted above, wherein distal bodies 112, 122 curve laterally in similar directions. Distal jaw bodies 112, 122 each further define opposing tissue-contacting surfaces 116, 126. Tissue-contacting surfaces 116, 126 are formed at least partially from an electrically-conductive material and either or both are adapted to connect to a source of energy as well as activation assembly 180 (FIGS. 6A-6C) via the lead wires extending through cable 2 (FIG. 1) to enable the selective supply of energy thereto for treating tissue grasped therebetween. Either or both of distal bodies 112, 122 may further define a knife channel 118, 128 extending through tissue-contacting surfaces 116, 126 to facilitate reciprocation of knife 162 between jaw members 110, 120.

Turning to FIGS. 1, 4, and 6A-6C, handle assembly 30 includes movable handle 40, fixed handle portion 50 of housing 20, and a linkage 44. Movable handle 40 is pivotably coupled to housing 20 within housing 20 to enable pivoting of movable handle 40 relative to fixed handle portion 50 between an initial position (FIG. 1) and a compressed position (FIG. 8A). Linkage 44 operably couples movable handle 40 with drive assembly 130 such that pivoting of movable handle 40 between the initial and compressed positions translates drive bar 132 (FIGS. 6C and 8B) through shaft 80 and relative to end effector assembly 100 to move jaw members 110, 120 between the spaced-apart position and the approximated position. Drive assembly 130 may further include a spring mandrel assembly 134 (FIGS. 6A-6C) operably coupling linkage 44 with drive bar 132 such that a closure pressure imparted to tissue grasped between jaw members 110, 120 is limited to a particular closure pressure range, e.g., between about 3 kg/cm² and about 16 kg/cm².

Movable handle 40 and fixed handle portion 50 further include cooperating engagement components 48, 58, respectively, e.g., a pin and corresponding track, to enabling locking of movable handle 40 in the compressed position upon achieving the compressed position, thereby retaining the jaw members 110, 120 in the approximated position. Cooperating engagement components 48, 58 may be disengaged, allowing movable handle 40 to return to the initial position, upon moving movable handle 40 further towards fixed handle portion 50 to an over-compressed position and then releasing or returning movable handle 40 towards the initial position.

With reference to FIGS. 1 and 4-6C, trigger assembly 60 includes a trigger 62, an elongated link 68a, and a lever arm 68b. Trigger 62 includes a toggle 63 and a disc body 66. Toggle 63 includes an upper flange 64a and a manipulation portion 65a extending from upper flange 64a. Upper flange 64a of toggle 63 includes disc body 66 rotatably coupled thereabout. Upper flange 64a further includes an activation post 64b extending from each lateral side thereof. As detailed below, one of the ends 64c of activation post 64b is configured to depress the corresponding switch 182 of activation assembly 180 (depending upon the direction of activation of trigger 62, as detailed below) to supply energy to jaw members 110, 120. Switches 182 may be configured as dome switches or other suitable switches to facilitate activation thereof via activation posts 64b. Switches 182 may be configured to produce an audible and/or tactile "click" upon activation, thus indicating to a user that energy is being supplied to end effector assembly 100 (FIG. 8B).

Manipulation portion 65a of toggle 63 of trigger 62 extends from housing 20 and defines a distally-facing contact surface 65b and a pair of side wing surfaces 65c extending from either side of distally-facing contact surface 65b in a proximal direction. Distally-facing contact surface 65b is configured to facilitate actuation of trigger 62, e.g., proximal pivoting of trigger 62 from an un-actuated position (FIG. 1) to an actuated position (FIG. 8B), to deploy knife 162 relative to end effector assembly 100 (see FIG. 8B). Side wing surfaces 65c are configured to facilitate activation of trigger 62, e.g., lateral pivoting of trigger 62 (in either lateral direction) from a neutral position (FIG. 1) to an activated position (FIG. 7), for urging one of the ends 64c of activation post 64b into the corresponding switch 182 of activation assembly 180 (depending upon the direction of activation of trigger 62) to activate the switch 182 and supply energy to jaw members 110, 120. Further, side wing surfaces 65c are configured to surround movable handle 40 in the initial position of movable handle 40 (see FIG. 4) such that lateral pivoting of trigger 62 from the neutral position is inhibited when jaw members 110, 120 are disposed in the spaced-apart position (see FIG. 1). As such, side wing surfaces 65c of trigger 62 and movable handle 40 cooperate to define a lockout that inhibits energy from being supplied to jaw members 110, 120 when jaw members 110, 120 are disposed in the spaced-apart position.

Figure 4:
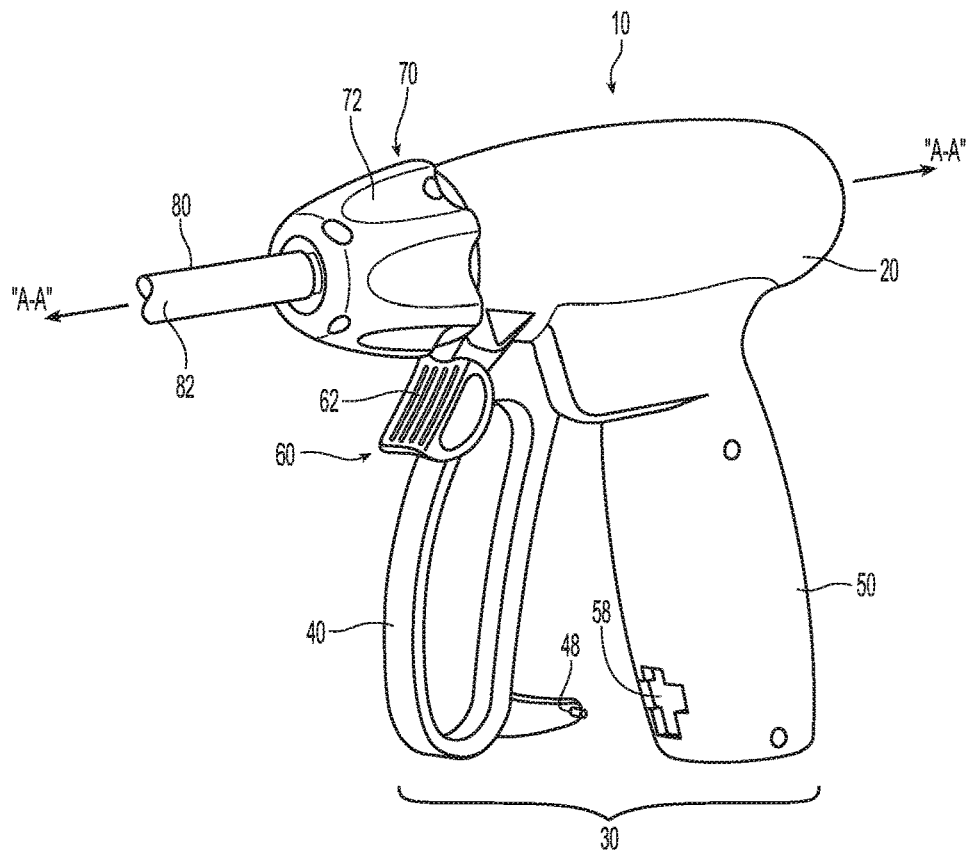
FIG. 4 is a perspective view of a proximal portion of the surgical forceps of FIG. 1.
Figure 5A:
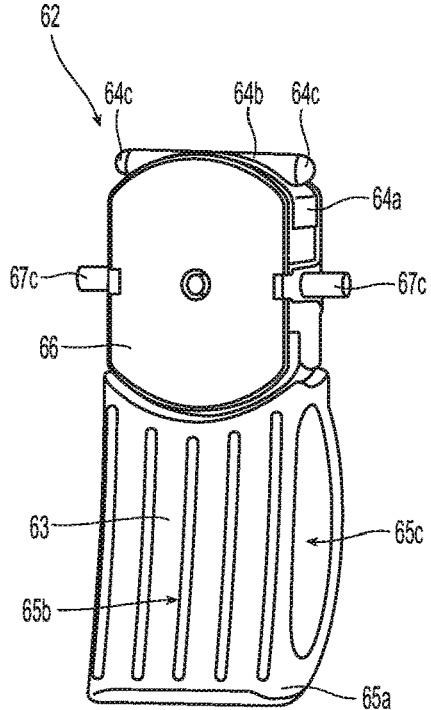
FIG. 5A is a front, perspective view of the trigger of the surgical forceps of FIG. 1.
Figure 5B:
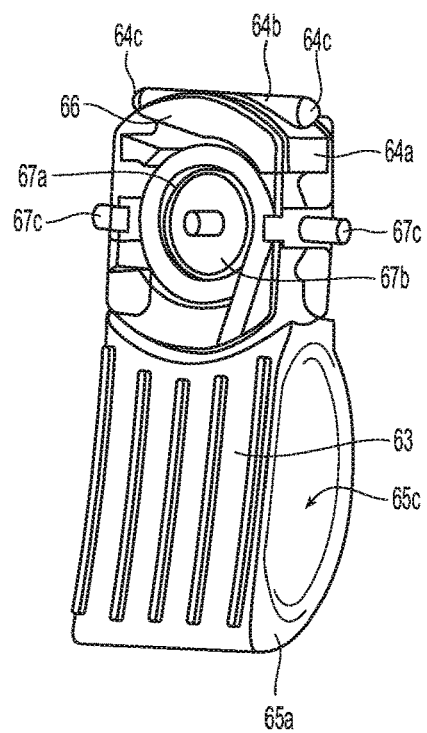
FIG. 5B is a rear, perspective view of the trigger of the surgical forceps of FIG. 1.
Figure 7:
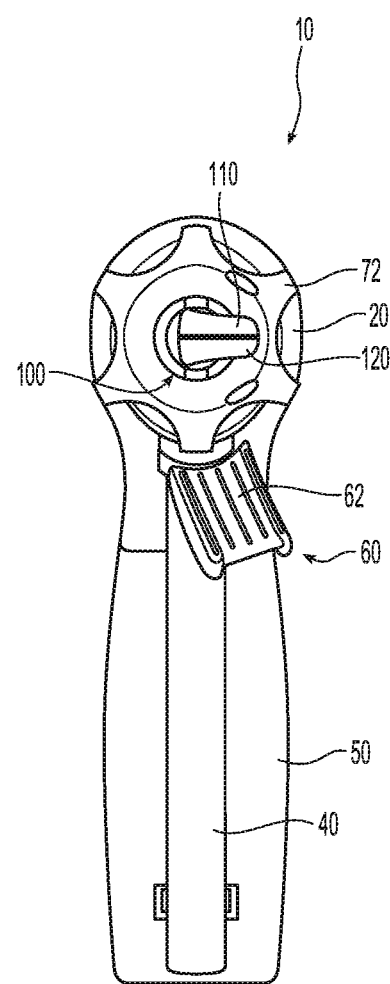
FIG. 7 is a front view of the surgical forceps of FIG. 1, with the trigger disposed in an activated position.

Disc body 66 of trigger 62, as noted above, is rotatably coupled about upper flange 64a. More specifically, disc body 66 includes a circular pivot aperture 67a received within a circular pivot member 67b defined within upper flange 64a of toggle 63 such that toggle 63 is laterally pivotable relative to disc body 66, e.g., between the neutral and activated positions (FIGS. 4 and 7, respectively). Disc body 66 further includes a pair of outwardly-extending pivot posts 67c configured for receipt within corresponding pivot apertures 22 (FIG. 6C, only one of apertures 22 is shown) defined within housing 20 to pivotably couple trigger 62 to housing 20. As such, trigger 62 is pivotably actuatable relative to housing 20, via the pivotable coupling of pivot posts 67c within pivot apertures 22, between the un-actuated position (FIG. 1) and the actuated position (FIG. 8A).

Referring to FIGS. 6A-6C, as noted above, trigger assembly 60 further includes an elongated link 68a and a lever arm 68b. Elongated link 68a is pivotably coupled to disc body 66 of trigger 62 at the distal end of elongated link 68a and is pivotably coupled to lever arm 68b at the proximal end of elongated link 68a. Lever arm 68b is pivotably coupled to housing 20 at a first end thereof, is operably coupled to proximal collar 164 of knife assembly 160 at a second end thereof. Proximal collar 164 is engaged about the proximal end of knife bar 166, which extends distally through housing 20 and a portion of shaft 80. Knife 162 (FIG. 8B) is engaged with and extends distally from knife bar 166. As a result of the above-detailed configuration, proximal actuation of trigger 62 from the un-actuated position (FIG. 1) to the actuated position (FIG. 8A) translates knife 162 distally to the extended position (FIG. 8B), wherein knife 162 extends between jaw members 110, 120.

As illustrated in FIGS. 6A and 6B, housing 20 may further define lock surfaces 24 positioned to interfere with activation post 64b of toggle 63 of trigger 62 in the activated position thereof such that actuation of trigger 62 from the un-actuated position to the actuated position is inhibited when trigger 62 is disposed in the activated position. Thus, knife 162 (FIG. 8B) is inhibited from being deployed while energy is being supplied to jaw members 110, 120 of end effector assembly 100 (see FIG. 8B). Likewise, when trigger 62 is disposed in the actuated position (FIG. 8A), activation posts 64b are positioned adjacent an interior surface of housing 20 and spaced-apart from switches 182, inhibiting lateral pivoting of trigger 62, thereby inhibiting energy activation when knife 162 is deployed.

Referring generally to FIGS. 1 and 4-8B, in use, once end effector assembly 100 is positioned adjacent an internal surgical site, e.g., through cannula 200 (FIGS. 2 and 3), as detailed above, forceps 10 may be manipulated, e.g., via moving housing 20 and/or rotating rotation nose 72 of rotation assembly 70, such that jaw members 110, 120 of end effector assembly 100 are positioned with tissue to be grasped, treated, and/or divided therebetween. Thereafter, jaw members 110, 120 may be moved from the spaced-apart position to the approximated position to grasp tissue by moving movable handle 40 from the initial position (FIG. 1) to the compressed position (FIG. 8A).

With tissue grasped between jaw members 110, 120 of end effector assembly 100, trigger 62 may be activated by laterally pivoting trigger 62 from the neutral position (FIG. 1) to either of the activated positions (e.g., the activated position illustrated in FIG. 7) to thereby activate the corresponding switch 182 of activation assembly 180. The activation of either switch 182 supplies energy from the energy source to tissue-contacting surfaces 116, 126 (FIG. 8B) of jaw members 110, 120 to treat tissue grasped therebetween.

Once tissue has been sufficiently treated, or where it is only desired to grasp and divide tissue, with trigger 62 disposed in (or returned to) the neutral position, trigger 62 may be pivoted proximally from the un-actuated position to the actuated position to thereby deploy knife 162 (FIG. 8B) between jaw members 110, 120 to cut tissue grasped therebetween. The treated and/or divided tissue may be released by releasing or returning movable handle 40 to the initial position and subsequent tissue may then be grasped, treated, and/or divided similarly as detailed above.

The above-detailed aspects and features of the present disclosure may be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 9:
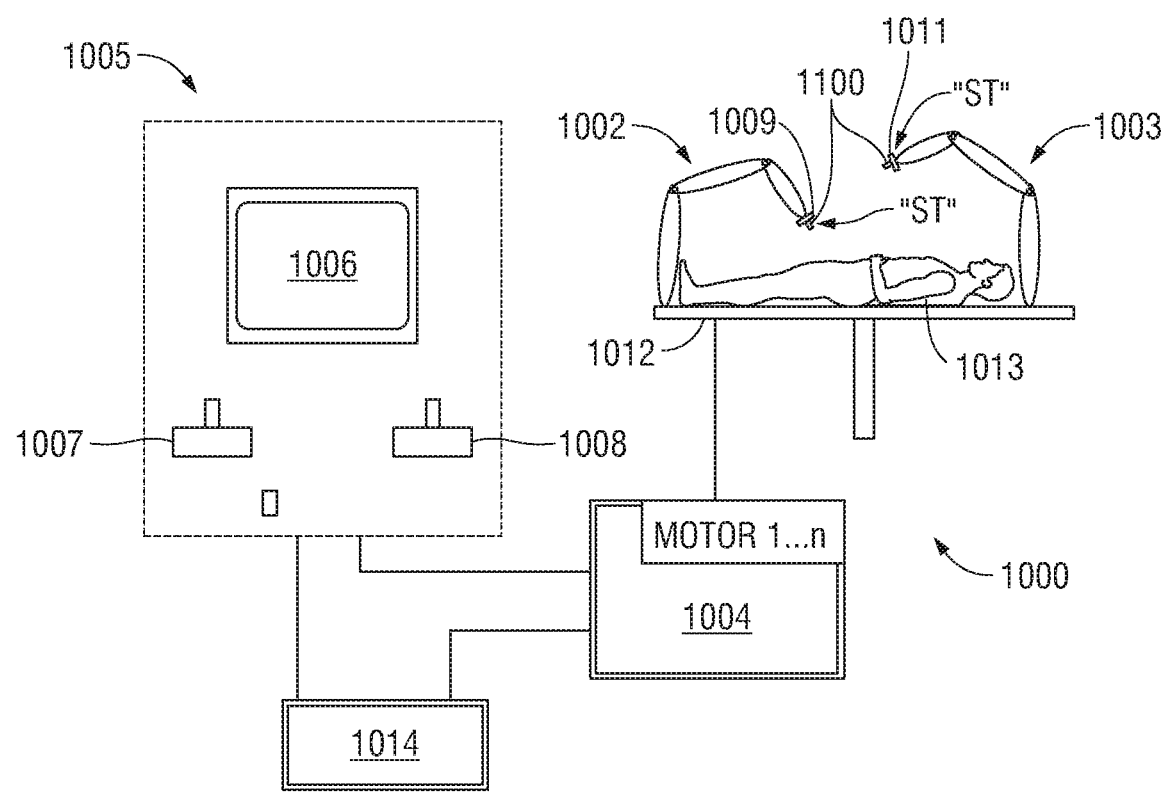
FIG. 9 is a schematic illustrating of a robotic surgical system configured for use in accordance with aspects of the present disclosure.

Turning to FIG. 9, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100. Suitable surgical tools "ST" include forceps 10, and end effector assembly 100 thereof (see FIG. 1).

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. A surgical instrument, comprising:
   a housing;
   a rotation knob supported by the housing, the rotation knob defining a distal end;
   an end effector assembly including first and second jaw members each defining a curved configuration, at least one of the first or second jaw members movable relative to the other between a spaced-apart position and an approximated position;
   a shaft extending between the housing and the end effector assembly, the shaft including:
      a proximal portion coupled with and extending distally from the distal end of the rotation knob, the proximal portion defining a proximal end portion and a distal end portion, the proximal portion defining a circular cross-sectional configuration to facilitate formation of a fluid-tight seal thereabout; and
      a distal portion extending distally from the proximal portion, a distal end of the distal portion longitudinally fixed relative to a proximal end of the end effector assembly, the distal portion defining a rectangular cross-sectional configuration to facilitate insertion through a cannula,
   wherein the circular cross-sectional configuration of the proximal portion of the shaft is substantially uniform between the proximal end portion and the distal end portion of the proximal portion of the shaft.

2. The surgical instrument according to claim 1, wherein the shaft is an integral, rigid component.

3. The surgical instrument according to claim 1, wherein the shaft further includes an intermediate portion interconnecting the proximal portion and the distal portion.

4. The surgical instrument according to claim 3, wherein the intermediate portion defines a smooth, continuous transition between the proximal portion and the distal portion.

5. The surgical instrument according to claim 1, wherein the distal portion of the shaft defines a pair of opposed long sides and a pair of opposed short sides.

6. The surgical instrument according to claim 5, wherein the first and second jaw members curve towards one of the opposed long sides of the distal portion of the shaft.

7. The surgical instrument according to claim 5, wherein lengths of the opposed long sides of the distal portion of the shaft approximate a diameter of the proximal portion of the shaft.

8. The surgical instrument according to claim 5, wherein lengths of the opposed short sides of the distal portion of the shaft are less than a diameter of the proximal portion of the shaft.

9. The surgical instrument according to claim 1, wherein the distal portion of the shaft is offset relative to the proximal portion of the shaft.

10. The surgical instrument according to claim 1, wherein the distal portion of the shaft is aligned with the proximal portion of the shaft.

11. A surgical system, comprising:
a cannula including a cannula housing, an elongated sleeve extending distally from the cannula housing, and a seal member disposed within the cannula housing; and
a surgical instrument configured for insertion at least partially through the cannula, the surgical instrument including:
a surgical instrument housing;
a rotation knob supported by the surgical instrument housing, the rotation knob defining a distal end;
an end effector assembly including first and second jaw members each defining a curved configuration, at least one of the first or second jaw members movable relative to the other between a spaced-apart position and an approximated position;
a shaft extending between the surgical instrument housing and the end effector assembly, the shaft including:
a proximal portion coupled with and extending distally from the distal end of the rotation knob, the proximal portion defining a proximal end portion and a distal end portion, the proximal portion defining a circular cross-section configuration, wherein the seal member is configured to form a fluid-tight seal about the proximal portion of the shaft upon insertion of the surgical instrument at least partially through the cannula; and
a distal portion extending distally from the proximal portion, a distal end of the distal portion longitudinally fixed relative to a proximal end of the end effector assembly, the distal portion of the shaft defining a rectangular cross-sectional configuration to facilitate insertion of the curved first and second jaw members through the cannula,
wherein the circular cross-sectional configuration of the proximal portion of the shaft is substantially uniform between the proximal end portion and the distal end portion of the proximal portion of the shaft.

12. The surgical system according to claim 11, wherein the shaft is an integral, rigid component.

13. The surgical system according to claim 11, wherein the shaft further includes an intermediate portion interconnecting the proximal portion and the distal portion, the intermediate portion defines a smooth, continuous transition between the proximal portion and the distal portion to facilitate insertion of the shaft through the seal member of the cannula.

14. The surgical system according to claim 11, wherein the cannula defines a lumen extending therethrough, the lumen having a first length, and wherein the distal portion of the shaft and the end effector assembly collectively define a second length that is equal to or greater than the first length.

15. The surgical system according to claim 14, wherein the first and second lengths are relatively configured such that, when the surgical instrument is inserted through the cannula with the end effector assembly of the surgical instrument extending distally from the cannula, the seal member of the cannula forms a fluid-tight seal about the proximal portion of the shaft of the surgical instrument.

16. The surgical system according to claim 11, wherein the distal portion of the shaft of the surgical instrument defines a pair of opposed long sides and a pair of opposed short sides, and wherein the first and second jaw members of the end effector assembly curve towards one of the opposed long sides of the distal portion of the shaft.

17. The surgical system according to claim 11, wherein the cannula defines a lumen extending therethrough, the lumen having a diameter, and wherein the proximal portion of the shaft and the end effector assembly define a maximum width dimension that is equal to or greater than the diameter of the lumen of the cannula.

18. The surgical system according to claim 17, wherein the surgical instrument is configured for insertion through the lumen of the cannula in an angled orientation relative to the lumen of the cannula to accommodate the curved first and second jaw members.

19. The surgical system according to claim 11, wherein the distal portion of the shaft is offset relative to the proximal portion of the shaft.

20. The surgical instrument according to claim 11, wherein the distal portion of the shaft is aligned with the proximal portion of the shaft.

* * * * *